US00PP14333P39

(12) United States Plant Patent
Zary

(10) Patent No.: US PP14,333 P3
(45) Date of Patent: Dec. 2, 2003

(54) CLIMBER ROSE PLANT NAMED JACETIMA

(50) Latin Name: *Rosa hybrida*
Varietal Denomination: JACetima

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/126,786

(22) Filed: Apr. 19, 2002

(65) Prior Publication Data

US 2003/0200584 P1 Oct. 23, 2003

(51) Int. Cl.[7] ..... A01H 5/00

(52) U.S. Cl. ..... Plt./115

(58) Field of Search ..... Plt./115

*Primary Examiner*—Bruce R. Campell
*Assistant Examiner*—Annette H. Para

(74) *Attorney, Agent, or Firm*—Klarquist Sparkman, LLP

(57) ABSTRACT

Climber rose plant having long climbing canes; flowers on new wood; repeats flowering; bright red flower color; ability to grown as a budded rose or on its own roots; and disease resistance.

1 Drawing Sheet

SUMMARY OF THE INVENTION

The present invention relates to a new and distinct variety of rose plant of the climber class which was originated by me by crossing the variety JACsat, U.S. Plant Pat. No. 8,741, with the variety JACpicl, U.S. Plant Pat. No. 9,492.

BACKGROUND OF THE INVENTION

The primary objective of this breeding was to produce a new rose variety having long, climbing canes, ability to flower on new wood, improved repeat flowering, a bright red flower color, good disease resistance and the ability to grow both as a budded plant and on its own roots.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Long climbing canes;
2. Flowers on new wood;
3. Repeats flowering;
4. Bright red flower color;
5. Ability to grow as a budded rose or on its own roots; and
6. Good disease resistance.

Asexual reproduction of this new variety by softwood and hardwood cuttings and budding on Dr. Huey roostock, as performed at Wasco, Calif., shows that the foregoing and all other characteristics and distinctions come true to form and are established and transmitted through succeeding propagations.

COMPARISON WITH PARENTS

As compared to JACsat, JACetima has smaller flowers of the same color as JACsat but without the latter's occasional varigations and has more bloom.

As compared to JACpicl, JACetima has a darker red flower color and the flowers have more petals.

COMPARISON WITH SIMILAR VARIETY

As compared to other red climbers, JACetima has improved repeat flowering, increased vigor and the ability to grow well as an own root plant.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) colour chart, except where ordinary dictionary significance of color is indicated.

Parentage:
*Seed parent.*—JACsat (U.S. Plant Pat. No. 8,741).
*Pollen parent.*—JACpicl (U.S. Plant Pat. No. 9,492).
Classification:
*Botanical.*—*Rosa hybrida.*
*Commercial.*—Climber.

FLOWER

Observations made from plants of two years of age grown in a garden environment at Somis, Calif., January to October, 2001.

Blooming habit: Continuous. Permanence: Outer petal edges curl slightly.

*Petalage.*—Number of petals under normal conditions: 30–35.

*Color.*—The upper sides of the petals are Red Group 45A with shading to Red Group 53A toward their base, with a spot of Yellow Group 4D at the base. The reverse sides of the petals are Red Group 53B shading to Red Group 53A toward their base. The major color on the upper side is Red Group 45A.

*Discoloration.*—The general tonality at the end of the first day: Red Group 45A. At the end of the third day: Red Group 45A. By the end of day five: Fades to Red Group 53C before petal drop.

*Fragrance.*—Slight. Character of fragrance: Soap.

Petals:

*Texture.*—Thick.

*Shape.*—Obovate.

*Margin.*—Undulate.

*Apex shape.*—Obtuse.

*Base shape.*—Cuneate.

*Form.*—Tips slightly recurved.

*Arrangement.*—Imbricated. Petaloids in the center are few (5–7). Petaloid Color: Red Group 45A.

*Persistence.*—Petals drop off cleanly before dyring.

*Lastingness.*—On the plant: Long (about 7–9 days). As a cut flower: Long (about 9–11 days).

Reproductive parts:

*Stamens.*—Number: 180–200. Anthers: Size: Length: 3–4 mm. Color: Yellow-Orange Group 20A.

Bud:

*Size.*—About 20–25 mm long when the petals start to unfurl.

*Form.*—The bud form is long, point ovoid.

*Color.*—When sepals first divide, bud color is Red Group 53B. When half blown, the upper sides of the petals are Red Group 45A with Red Group 53A at base; and the lower sides of the petals are Red Group 53B with Red Group 53A at base.

*Sepals.*—Color: Upper surface: Green Group 143C. Lower surface: Green Group 144A. Length: 22–28 mm. Width: 9–12 mm. Shape: Subulate. Surface texture: Upper: Incanous. Lower: Glandular. There are three normally appendaged sepals. There are two unappendaged sepals with hairy edges.

*Receptacle.*—Color: Yellow-Green Group 146C. Shape: Funnel. Size: Long, about 12–14 mm×7–9 mm. Surface: Smooth with some fine hairs.

*Peduncle.*—Length: Medium, averaging about 70–90 mm. Surface: Glandular. Color: Yellow-Green Group 145A. Strength: Erect, slender.

Bloom:

*Size.*—Medium. Average open size is 8–10 cm.

*Borne.*—In pyramidal clusters of 5–9 blooms.

*Stems.*—Strength: Strong. Average length is about 30–40 cm.

*Form.*—When first open: High centered. Arrangement: Regular around styles. Filaments: Color: Yellow-Orange Group 21C at base; Red Group 40B at top. Pollen: Color: Greyed-Orange Group 167C.

*Pistils.*—Number: 150–170. Styles: Color: Yellow Group 2D at base, Red Group 52C at top. Length: 7–10 mm. Stigmas: Color: Greyed-Yellow Group 162D. Length: 1–2 mm.

*Hips.*—Color: Yellow-Green Group 144B with Greyed-Purple. Group 184B blush. Shape: Pear. Size: 12–18 mm long×10–16 mm wide.

Plant:

*Form.*—Climber.

*Growth.*—Vigorous, upright and branching.

*Mature plant.*—Height: 3–5 m. Width: 3–5 m.

*Canes.*—Length: 2–5 m.

Foliage: Number of leaflets on normal mid-stem leaves: 5–7.

*Size.*—Length: 14–16 cm. Width: 10–12 cm.

*Quantity.*—Normal.

*Color.*—New foliage: Upper side: Green Group 137C. Lower side: Yellow-Green Group 146C. Old foliage: Upper side: Green Group 137A. Lower side: Yellow-Green Group 146B.

Leaflets:

*Size.*—Length: 40–60 mm. Width: 20–35 mm.

*Shape.*—Ovate.

*Base shape.*—Cuneate.

*Apex shape.*—Acute.

*Texture.*—Glossy, smooth.

*Edge.*—Serrated.

*Serrations.*—Single, small.

*Petiole color.*—Yellow-Green Group 145A.

*Petiole rachis.*—Color: Yellow-Green Group 145A. Petiole Underside: Smooth with very fine hairs.

*Auricle shape, if present.*—Not present.

*Stipules.*—Short, serrated (about 24–28 mm long, bearded).

*Disease resistance.*—Susceptible to mildew; resistant to blackspot and rust under normal growing conditions.

*Pest persistance.*—Not tested.

Wood:

*New wood.*—Color: Greyed-Red Group 178A. Bark: Smooth with fine hairs at top of stem.

*Old wood.*—Color: Yellow-Green Group 146C. Bark: Smooth with fine hairs at top of stem.

Prickles:

*Quantity.*—On main canes from base: Many. On laterals from main canes: Ordinary.

*Form.*—Hooked slightly downward. Length: 6–8 mm.

*Color when young.*—Greyed-Purple Group 184A.

*Color when mature.*—Greyed-Purple Group 174B.

Small prickles:

*Quantity.*—On main stalks: None. On laterals: None.

Winter hardiness: Hardy to Zone 5.

I claim:

1. A new and distinct variety of rose plant of the climber class, substantially as herein shown and described, characterized particularly by long climbing canes; flowers on new wood; repeats flowering; bright red flower color; ability to grow as a budded rose or on its own roots; and good disease resistance.

* * * * *

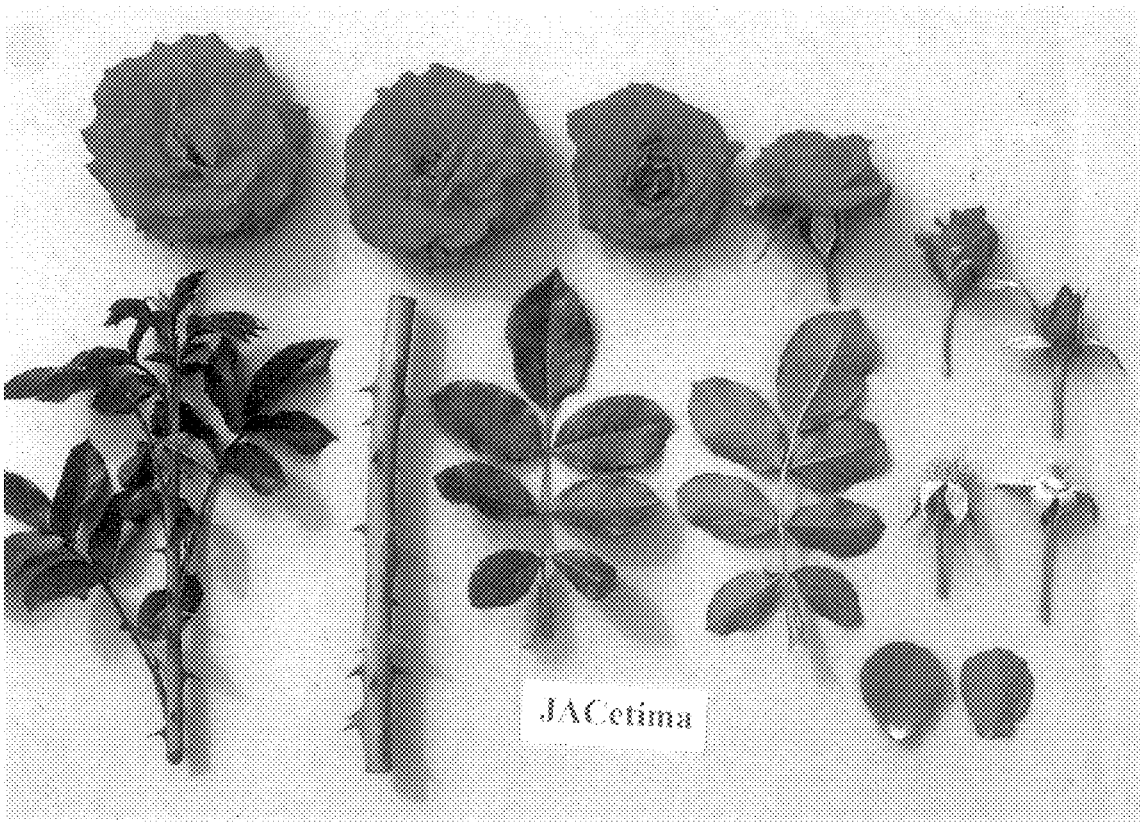
JACetima

UNITED STATES PATENT AND TRADEMARK OFFICE

CERTIFICATE OF CORRECTION

PATENT NO. : PP 14,333 P3
DATED : December 2, 2003
INVENTOR(S) : Zary

It is certified that error appears in the above-identified patent and that said Letters Patent is hereby corrected as shown below:

Column 3,
Lines 5-34, beginning with the word "Permanence:" through the word "20A" should be deleted and inserted in Column 4 between lines 1 and 2.

Column 4,
Line 1, reads "*Form.*—When first open: High centered.
Arrangement:" should read -- *Form.* When first open: High centered. --

Signed and Sealed this

Eleventh Day of May, 2004

JON W. DUDAS
*Acting Director of the United States Patent and Trademark Office*